United States Patent [19]
Turner

[11] Patent Number: 5,194,731
[45] Date of Patent: Mar. 16, 1993

[54] INDUCTIVELY COUPLED PLASMA SPECTROSCOPY

[75] Inventor: Ian L. Turner, Reservoir, Australia

[73] Assignee: Varian Associates, Inc., Palo Alto, Calif.

[21] Appl. No.: 734,852

[22] Filed: Jul. 23, 1991

[30] Foreign Application Priority Data

Jul. 24, 1990 [AU] Australia .............................. PK1341

[51] Int. Cl.⁵ ...................... B01D 59/44; H01J 49/00; H01J 17/00
[52] U.S. Cl. .............................. 250/281; 315/111.51; 315/111.81
[58] Field of Search ................ 250/281, 288; 315/111.51, 111.81, 248

[56] References Cited

U.S. PATENT DOCUMENTS

| | | | |
|---|---|---|---|
| Re. 33,386 | 10/1990 | Douglas | 315/111.81 |
| 4,501,965 | 2/1985 | Douglas | 250/281 |
| 4,682,026 | 7/1987 | Douglas | 315/111.81 |
| 4,849,675 | 7/1989 | Muller | 315/111.81 |
| 4,982,140 | 1/1991 | Witting | 315/111.51 |

FOREIGN PATENT DOCUMENTS

0261338 7/1987 European Pat. Off. .

OTHER PUBLICATIONS

Stark, D. S. et al. "Ion Analysis of RF-Excited Deuterium Ion Sources," *Nuclear Instruments and Methods in Physics Research*, v. 91, No. 3, Feb. 1971, pp. 301-305.

Primary Examiner—Bruce C. Anderson
Attorney, Agent, or Firm—Edward H. Berkowitz

[57] ABSTRACT

In inductively coupled plasma spectroscopy, the use of an induction coil assembly comprising at least two helical coils which are arranged in overlapping relationship. In one practical form, the overlap is achieved by interlacing of the coils so that at least one turn of one coil is interposed between two adjacent turns of the other coil. For that purpose, the two coils will ideally be of the same diameter and will be coaxial. A tubular part of a plasma torch is contained within the space surrounded by the coil assembly, and a RF energy source is connected to an end of each coil. The other ends of the coils may be connected to ground.

22 Claims, 3 Drawing Sheets

INDUCTIVELY COUPLED PLASMA SPECTROSCOPY

BACKGROUND OF THE INVENTION

This invention relates to inductively coupled plasma spectroscopy, and more particularly to the means for sustaining, and possibly generating an inductively coupled plasma in a spectrometer for use in chemical analysis. It will be convenient to hereinafter describe the invention with particular reference to mass spectrometers, but the invention is not limited to that application and may be used in other spectrometers such as optical emission spectrometers.

An inductively coupled plasma mass spectrometer should be able to detect the presence of very low levels of chemical elements in samples being tested. To achieve this end, the apparatus is provided with an inductively coupled plasma torch and induction coil means for sustaining a plasma by coupling radio frequency electro-magnetic energy into a suitable gas, typically argon, flowing through the plasma torch. The combination of an inductively coupled plasma torch and induction coil means for sustaining a plasma can be referred to as an inductively coupled plasma source.

A sample for analysis in a mass spectrometer is introduced into the inductively coupled plasma by known means. Chemical elements in the sample are atomised and ionized, and the apparatus responds to the ions so produced by generating signals which are characteristic of particular chemical elements. The output of the apparatus also contains a background signal which may arise from a number of effects including light, excessively energetic ions or excited neutral atoms reaching the detector of the mass spectrometer, and background electrical signals inevitably present in such apparatus.

To permit the detection of very low levels of chemical elements in samples being tested, the ion signals produced by chemical elements should be large compared to the background signal in the output of the apparatus, so that signals arising from chemical elements may readily to distinguished from fluctuations in the background signal.

Various inductively coupled plasma sources are known to be useful in inductively coupled plasma mass spectrometers, and are distinguished principally by the configuration of the induction coil means used for sustaining the plasma. In one particular prior art arrangement, the radio frequency energy is applied to one end of the coil and the other end of the coil, nearest the mass spectrometer interface, is grounded. This is known as the front-grounded coil. In another prior arrangement, the coil is supplied with radio frequency energy at its two ends and is grounded at the centre. This latter arrangement is sometimes referred to as a centre-grounded coil and is described in U.S. Pat. No. 4,501,965.

The prior induction coils referred to above are not entirely satisfactory in operation. In particular, the prior coils retune at a relatively slow rate under some operating conditions, and do not have sufficiently efficient power coupling characteristics. Both aspects are thought to be due to the relevant coil having an inadequate electrical coupling coefficient.

SUMMARY OF THE INVENTION

It is an object of the present invention to provide an induction coil assembly for an inductively coupled plasma source, having a relatively high coupling coefficient. In particular, the coil assembly of the present invention has the capacity to retune at a relatively fast rate under various operating conditions, and enables efficient use of power. It is a further object of the invention to provide an improved inductively coupled plasma spectrometer.

In accordance with one aspect of the invention, there is provided an induction coil assembly for use in an inductively coupled plasma spectrometer, including at least two helical coils which are relatively arranged so as to be in at least partial overlap, one end of each said coil being connectable to a high frequency energy source, and the other end of each said coil being connectable to ground.

In accordance with another aspect of the invention, there is provided an inductively coupled plasma spectrometer including, a plasma torch, a tube for at least partially containing the plasma, an induction coil assembly surrounding said tube and being operable to sustain the plasma, said assembly being composed of at least two helical coils, at least part of at least one turn of one said coil having an overlap with at least part of a turn of the other said coil, one end of each said coil being connectable to a high frequency energy source, and detection means which is operable to detect the presence of a selected element or elements within said plasma.

The overlap between the two coils is conveniently achieved by interlacing of the coils. That is, at least one turn of one coil is interposed between two adjacent turns of the other coil. Ideally, each turn but one of the first coil is interposed between a respective two adjacent turns of the other coil. Such an arrangement optimises the coupling between the coils, and also minimises the axial length of the coil assembly. An interlacing arrangement is effective in operation and has the advantage of compactness in both the radial and the axial directions. It will usually be the case that, in such an arrangement, the two coils are of substantially the same diameter, are coaxial, and are of substantially the same axial length, but none of those relationships is essential to satisfactory performance of the coil assembly.

A satisfactory coil assembly might involve two coils of different diameter, with the smaller diameter coil being located within the space surrounded by the larger diameter coil. In such an arrangement, a turn of the smaller coil may not intrude between adjacent turns of the larger coil, so that the overlap is axial in nature. The level of performance of such a coil assembly is expected to be at an optimum when the outer diameter of the smaller coil is not significantly less than the inner diameter of the larger coil. It will be appreciated that, in such an arrangement, the hand of twist of one coil may be opposite to that of the other.

In one particular form of the preferred interlaced arrangement, one end of one coil is connected to the remote end of the other coil so that the coils are in effect connected in series. The resulting coil assembly may be driven by a RF energy source connected to each of the other two ends of the coils. In another form of the interlaced arrangement, the two coil ends not connected to the RF source, are mechanically independent of one another.

Embodiments of the invention are described in detail in the following passages of the specification which refer to the accompanying drawings. The drawings, however, are merely illustrative of how the invention might be put into effect, so that the specific form and arrangement of the various features as shown is not to be understood as limiting on the invention.

DETAILED DESCRIPTION OF THE INVENTION

Figure 1:
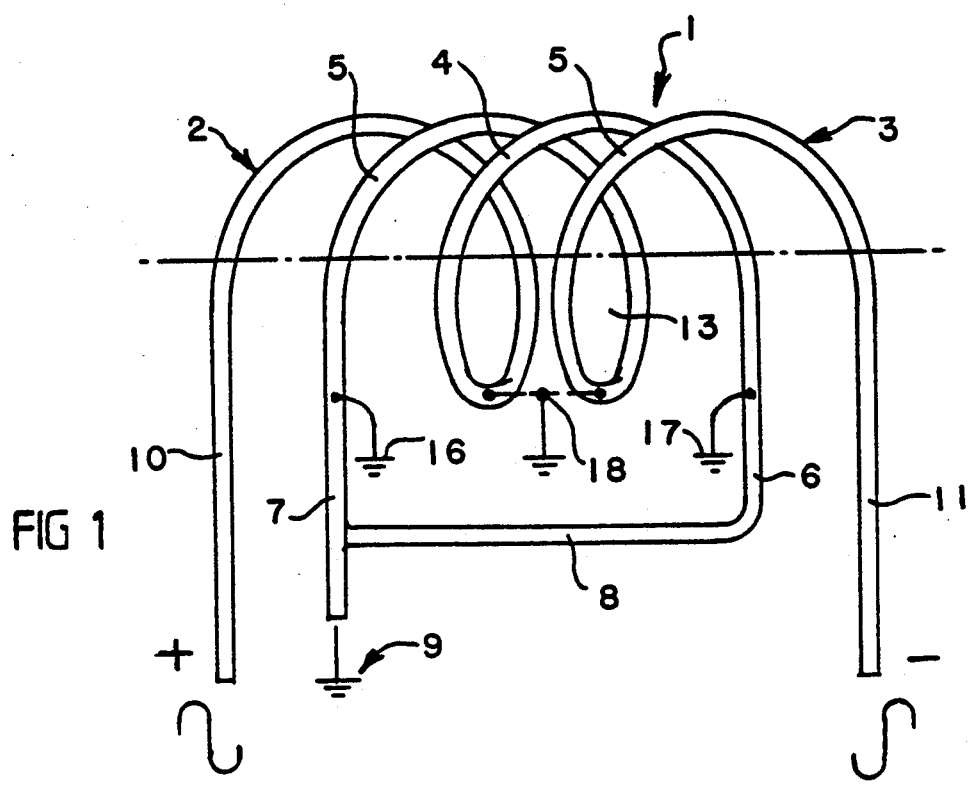
FIG. 1 is a diagrammatic representation of an induction coil assembly according to one embodiment of the invention.

The coil assembly 1 shown in FIG. 1 of the drawings is suitable for use in an inductively coupled plasma spectrometer, and is formed of two coils 2 and 3 arranged in overlapping relationship. Each of the coils 2 and 3 is helically wound so as to have the same hands of twist and the same pitch between turns, but other arrangements are possible. The two coils 2 and 3 overlap as a consequence of being interlaced. That is, at least one turn 4 of the coil 2 is interposed between two adjacent turns 5 of the coil 3. In that regard, it is preferred that the spacing between adjacent turns 4 and 5 is substantially equal to one half of the coil pitch. It is also preferred that the coils 2 and 3 are of substantially the same diameter and are substantially coaxial, as shown.

In the particular arrangement shown in FIG. 1, the end 6 of the coil 2 is connected to the remote end 7 of the coil 3, so that the two coils are in effect connected in series. The connection between the coil ends 6 and 7 is represented by the member 8, and the connected ends may be grounded as represented by reference 9. The other ends 10 and 11 of the two coils 2 and 3 may function as or be connected to terminals for connecting to a radio frequency (RF) or other high frequency energy source as represented by reference 12 in FIG. 3 of the drawings. The radio frequency source 12 is preferably balanced, but that is not essential as will be made clear herebelow.

Figure 3:
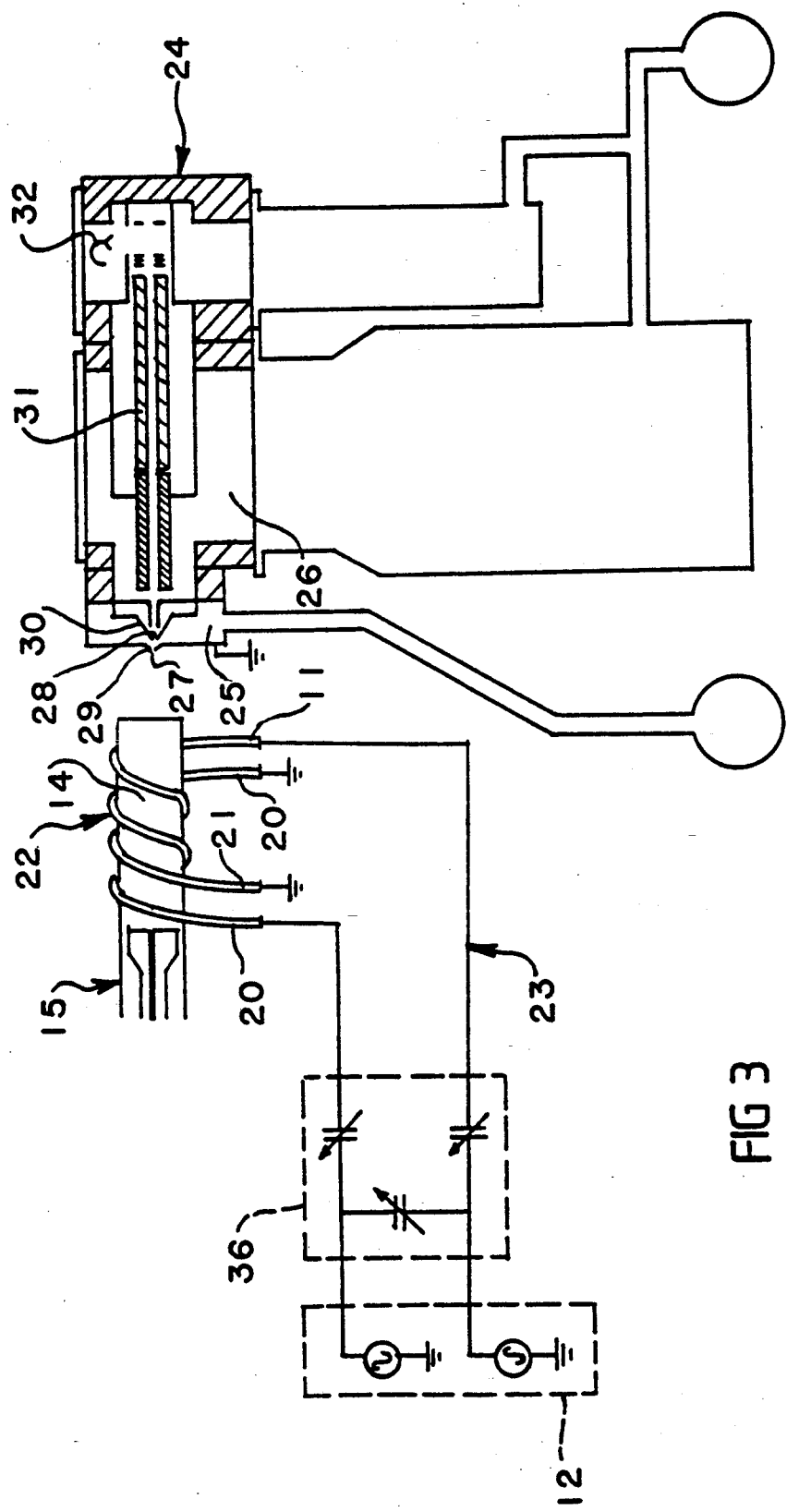
FIG. 3 is a diagrammatic representation of an inductively coupled plasma mass spectrometer including a coil assembly according to the present invention.

The coil assembly 1 of FIG. 1 surrounds a cylindrical space 13 which, in use, may contain a tube 14 of a plasma torch 15 as shown diagrammatically in FIG. 3. The plasma may be initiated by any known means, and ions formed in the plasma will experience three electrical "earths" or "grounds" along the length of the cylindrical space 13. The first and second "grounds" (numbered 16 and 17 in FIG. 1) are formed because the coil ends 6 and 7 are in direct electrical contact with the ground connection 9. A third "ground" is formed midway along the length of the coil assembly 1 as indicated by numeral 18 in FIG. 1.

In circumstances where a balanced RF source is connected to the terminals 10 and 11, the third "ground" 18 of FIG. 1 is an apparent or virtual ground created because the coil turns 4 and 5 on either side of the virtual ground 18 are charged at any one time with potentials of opposite sign but identical magnitude. That is, a virtual ground will be created at a point approximately midway between the turns 4 and 5 and will remain at ground potential even though the potentials of the turns 4 and 5 change continuously.

The configuration of the coils 2 and 3 shown in FIG. 1, produces three types of electromagnetic fields within the cylindrical space 13 surrounded by the coil assembly 1. These electromagnetic fields each impart energy to the ions formed in the plasma, and it is believed that the interaction of these electromagnetic fields with the ions results in the ions having energies favourable to the sampling of the ions and subsequent analysis thereof by a mass spectrometer.

Firstly, the current in the coil assembly 1 induces magnetic fields directed along the axis of the coil assembly 1. Secondly, those axial magnetic fields induce transaxial electric fields. Thirdly, a voltage proportional to the driving frequency (that is, proportional to the rate of change of the current) is induced along the coil assembly 1, and produces an axial electric field component. When the coils 2 and 3 are driven by a balanced radio frequency source, the geometry of the interlaced coils 2 and 3 superimposes the fields from each of the two coils, with the result that some components of the electromagnetic fields are mutually reinforced while other components are cancelled out, at least to some extent.

The extent of the interaction between the electromagnetic fields of the two coils 2 and 3 of FIG. 1 is indicated by the electrical coupling coefficient, k, of the coil assembly 1. The coupling coefficient of an assembly 1 as shown in FIG. 1 has been measured at 0.58. That value is relatively high compared to the value of 0.37 which has been measured for the centre-grounded induction coil as disclosed by U.S. Pat. No. 4,501,965, and is very high compared to the coupling coefficient of 0 which is characteristic of front-grounded or rear-grounded induction coils.

Although FIG. 1 shows a ground connection 9 to which each of the two coil ends 6 and 7 are connected, it is not essential that the two coils 2 and 3 be grounded in that way. In some circumstances the coil assembly 1 may operate effectively without any ground connection. When the radio frequency source is balanced, and the coils 2 and 3 are of the same configuration, the connector 8 will in any event be at ground potential or close to ground potential. Thus, in those circumstances, it should not be necessary to force the connector 8 to ground potential by providing the ground connection 9. It may be convenient however, to provide the ground connection 9 so that the connection 8 is maintained at ground potential in circumstances where the radio frequency source is less than perfectly balanced.

Figure 2:
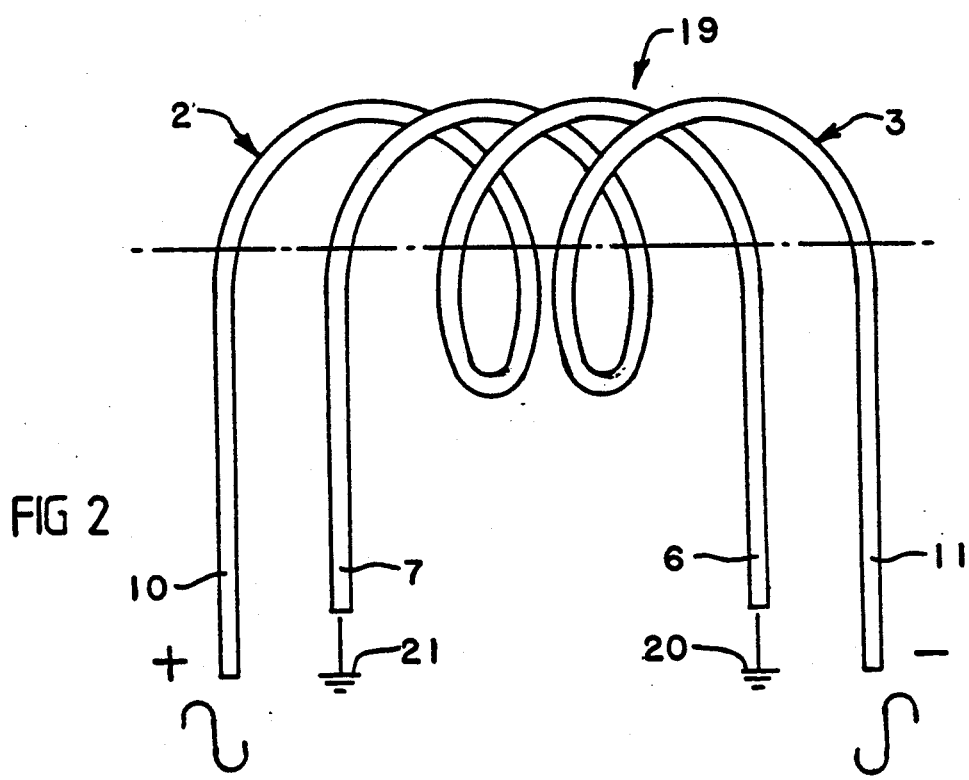
FIG. 2 is a diagrammatic representation of an induction coil assembly according to another embodiment of the invention.

The coil assembly 19 shown in FIG. 2 is very similar to that of FIG. 1. The only difference is that the coils 2 and 3 of the assembly 19 are mechanically independent of each other, and the coil ends 6 and 7 are independently grounded as indicated at 20 and 21.

The coils 2 and 3 of both assemblies as shown in FIGS. 1 and 2, may be made from hollow tubing. In use, each coil may be cooled by passing a suitable coolant such as water through its bore. An advantage of the mechanically independent coils 2 and 3 of FIG. 2, is that they can be separately cooled, and that could be important in circumstances where the bore of one coil become blocked.

FIG. 3 shows, in diagrammatic form, how a coil assembly according to the invention can be used in an inductively coupled plasma mass spectrometer. The coil assembly 22 is connected into a circuit 23 which includes a balanced radio frequency source 12. The coil assembly 22 is connected into the circuit 22 by way of terminals 10 and 11, and is grounded at 20 and 21. The mass spectrometer 24 includes a first vacuum chamber 25 and a second vacuum chamber 26, each of which has an orifice 27 and 28 respectively through which ions to be sampled can pass. The orifices 27 and 28 are formed in cones 29 and 20 respectively, each of which is grounded. The ions that pass through the orifices 27 and 28 are analysed in a mass analyser 31 in known manner, and detection means 32 operates in a known manner to detect elements of interest.

Figure 4:
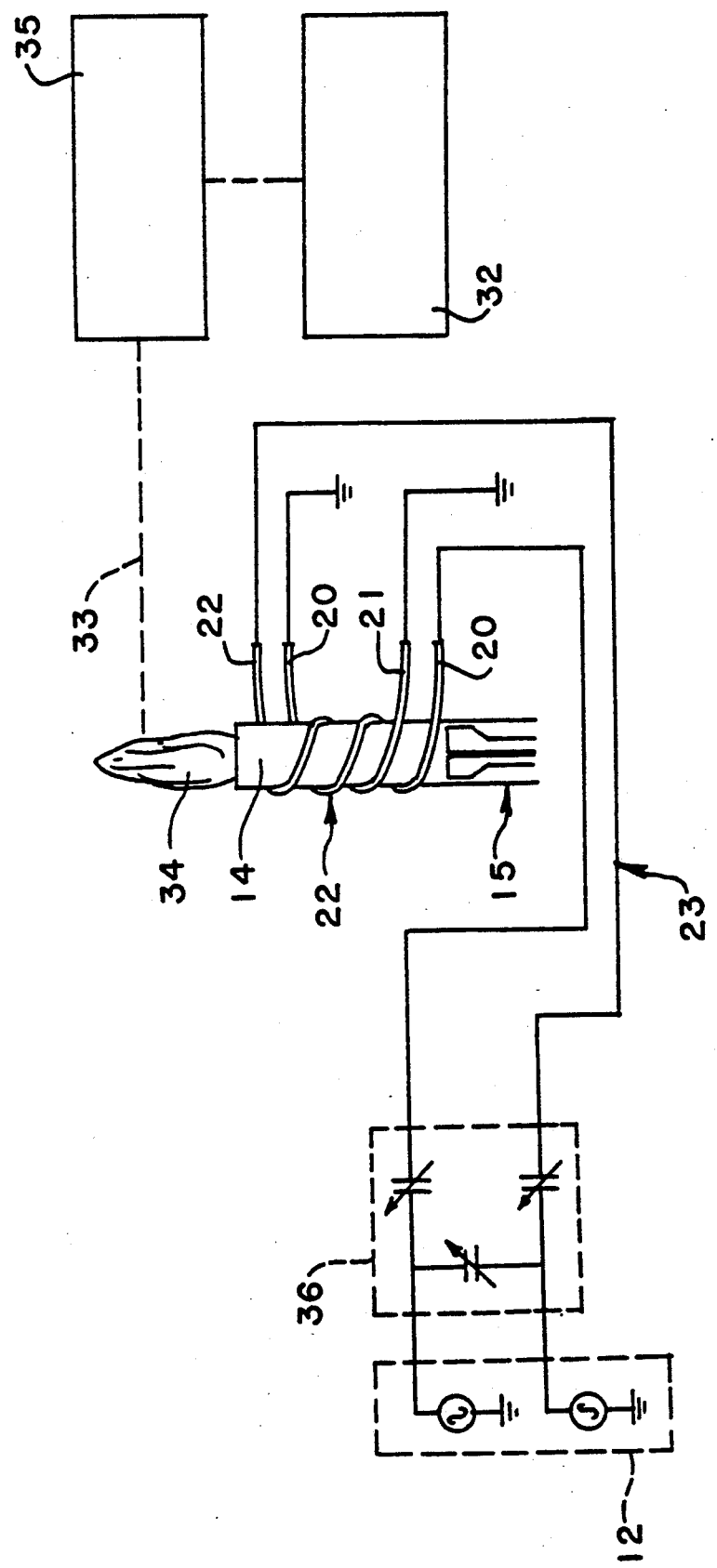
FIG. 4 is a diagrammatic representation of an inductively coupled plasma emission spectrometer including a coil assembly according to the present invention.

FIG. 4 shows, in diagrammatic form, use of a coil assembly according to the invention in an inductively coupled plasma emission spectrometer. Components of that apparatus which correspond to components of the FIG. 3 apparatus, have been given like reference numerals. Emissions characteristic of the element or elements of interest travel along the path 33 from the plasma 34 and are isolated from other emissions by a monochromator 35 which is connected to the detection means 32.

In each of the arrangements of FIGS. 3 and 4, the circuit 23 preferably includes an impedance matching network 36.

Tests have indicated that a plasma system incorporating an interlaced coil assembly of the kind described, rather than a center tapped coil, is better suited for use in circumstances where the plasma load conditions change—e.g., as a consequence of introduction of organics. In particular, it is found that the interlaced coil system re-tunes at a rate faster than a center tapped coil system. Furthermore, if the RF generator is a free running oscillator, an interlaced coil is able to sustain a heavily loaded plasma which is beyond the capacity of a center tapped coil. That is due to the higher coupling coefficient of the interlaced coil assembly.

Tests have also been conducted to determine the effective power coupling (i.e., the ratio of power delivered to the coil compared to power delivered to the plasma) of the interlaced system and the center tapped system. A UV radiometer was used to detect emitted UV light from the plasma. The UV light emitted from a plasma is proportional to the temperature of the plasma. Increasing the power coupled into the plasma increases the temperature of the plasma, and hence the UV light emitted. It was found that for a fixed RF input power, more UV light was emitted from the plasma for the interlaced induction system than for the center tapped induction system. That indicates that the coupling of power from the induction system to the plasma is higher for the interlaced coil assembly than for the center tapped coil, and the result is believed to be because of the increased coupling coefficient of the interlaced assembly.

Comparative testing has also been conducted between previously known induction coils and the induction coil assembly of the present invention. In each case, the same mass spectrometer was used with the same test sample, and the variable parameters of the apparatus were optimised for each of the induction coils. The figure of merit used for the comparison was the limit of detection for the element strontium. This element was present in the test sample at a known concentration, and the limit of detection was calculated from the measured ion signal corresponding to the most abundant strontium isotope (mass number 88) and the statistical fluctuations in the background signal, according to generally accepted procedures.

When fitted with a front-grounded induction coil the apparatus achieved a limit of detection for strontium of 900 parts per million million. When equipped with a centre-grounded induction coil, the apparatus achieved a limit of detection for strontium of 60 parts per million million. When the coil assembly of the invention was installed in the apparatus, the limit of detection for strontium was 6 parts per million. Accordingly, this indicated that under at least some conditions the coil assembly of the present invention is able to produce analytical performance which is better by a factor of ten over that obtained with the centre-grounded coil described in U.S. Pat. No. 4,501,965. Other sample materials and other test elements may give different results. The mass spectrometer used in the aforementioned tests did not have multicomponent ion lenses, or means to prevent light, or excessively energetic ions, or excited neutral atoms from entering the mass spectrometer. It may be that a coil assembly as described herein would further improve the analytical performance of apparatus equipped with such devices.

In some circumstances in the analysis of ions by a mass spectrometer it may be desirable to vary the energies of the ions, even though that would possibly be at the expense of the ion signal to background signal ratio. By way of example, such variation may be desirable to minimise the formation of refractory oxide ions, or other polyatomic ions, in a particular analysis. Such variation may also be desirable to control the formation of double charged ions in an analysis. It may therefore be of benefit that variation of ion energies may be achieved by varying the radio frequency energy applied to one of the two coils which make up the coil assembly of the present invention. The electromagnetic properties of the coil assembly would alter in those circumstances, leading to different ion energies. Clearly, a relatively simple electronic device could be inserted into the circuit 23 shown in FIGS. 3 or 4 so as to permit variation of the electromagnetic energy supplied to the terminals 10 and 11. The electronic device could be adjusted until the spectrum produced by the apparatus indicated that the desired reduction in polyatomic ions, or control of the formation of doubly charged ions, had been achieved.

It is to be understood that coil configurations other than those shown by FIGS. 1 and 2 are possible. It is not, for example, essential that the two overlapping coils be of the same diameter. It is also not necessary to effect the overlapping by interlacing as herein particularly described. An alternative configuration which may produce satisfactory analytical results is a coil assembly wherein a first coil has a greater diameter than a second coil, and the second coil is at least partially located within the central space of the first coil. Since the two coils in this configuration are not interlaced they may be wound in opposite handed senses should this produce better analytical performance.

Various other alterations, modifications and/or additions may be introduced into the constructions and arrangements of parts previously described without departing from the spirit or ambit of the invention as depicted by the appended claims.

Having now described my invention, what I claim as new and desire to secure by Letters Patent is:

1. An induction coil assembly for use in an inductively coupled plasma spectrometer, including at least two helical coils which are relatively arranged so as to be in at least partial overlap, one end of each said coil being connectable to a high frequency energy source, and the other end of each said coil being connectable to ground.

2. A coil assembly according to claim 1, wherein said high frequency source is a radio frequency source.

3. A coil assembly according to claim 1, wherein both said coils surround a space for receiving at least part of a plasma torch.

4. A coil assembly according to claim 1, wherein at least one of said coils has two or more turns, and said overlap is effected as a result of at least part of at least one turn of one said coil being interposed between two adjacent turns of the other said coil.

5. A coil assembly according to claim 4, wherein the two said coils are coaxial, are of substantially the same diameter, and are interlaced so that at least one turn of one said coil is interposed between two adjacent turns of the other said coil.

6. A coil assembly according to claim 5, wherein each said turn of said one coil is interposed between a respective two adjacent turns of said other coil.

7. A coil assembly according to claim 1, wherein the said other ends of said coils are connected together.

8. A coil assembly of claim 1 wherein said ground is a virtual ground.

9. A plasma torch assembly including a tube for containing the plasma, at least two helical induction coils surrounding said tube, said coils being in at least partially overlapping relationship, one end of each said coil being connectable to a high frequency source, each said one end being at a respective opposite end of the assembly formed by said coils, and the other end of each said coil being connectable to ground.

10. A torch assembly according to claim 9,, wherein the two said coils are coaxial, are of substantially the same diameter, and are interlaced so that at least one turn of one said coil is interposed between two adjacent turns of the other said coil.

11. An inductively coupled plasma spectrometer including a torch assembly according to claim 9.

12. The plasma torch assembly of claim 9 wherein said ground is a virtual ground.

13. An induction coil assembly for use in an inductively coupled plasma spectrometer, including at least two helical coils which are relatively arranged so that at least part of at least one turn of one said coil overlaps at least part of a turn of the other said coil, one end of each said coil being connectable to a high frequency energy source, each said one end being at a respective opposite end of said assembly, and the other end of each said coil being connectable to ground.

14. A coil assembly according to claim 13, wherein said overlap involves said one turn of said one coil being at least partially interposed between two adjacent turns of the other said coil.

15. An inductively coupled plasma spectrometer including, a plasma torch, a tube for at least partially containing the plasma, an induction coil assembly surrounding said tube and being operable to sustain the plasma, said assembly being composed in at least two helical coils, each said coil having two ends, at least part of at least one turn of one said coil having an overlap with at least part of a turn of the other said coil, one end of each said coil being connectable to a high frequency energy source, the other ends of the respective coils being connected together, and detection means which is operable to detect the presence of a selected element within said plasma.

16. A spectometer according to claim 15, wherein said overlap is effected by said one turn of said one coil being at least partially interposed between two adjacent turns of said other coil.

17. A spectrometer according to claim 16, wherein a plurality of turns of said one coil are each interposed between a respective two adjacent turns of said other coil.

18. A spectrometer according to claim 15, wherein the said energy source connectable to one said coil is substantially 180° out of phase with the said energy source connectable to the other said coil.

19. A spectrometer according to claim 15, being in the form of a mass spectrometer and wherein the energy source connectable to said assembly is substantially balanced between the two said coils.

20. A spectrometer according to claim 15, being in the form of an emission spectrometer and wherein the energy source connectable to said assembly is substantially balanced between the two said coils.

21. The inductively coupled plasma spectrometer of claim 15 wherein said coils are grounded by a virtual ground.

22. The inductively coupled plasma spectrometer of claim 15 wherein said connection between said coil ends is a connection through ground.

* * * * *